(12) United States Patent
Prudence et al.

(10) Patent No.: US 10,471,041 B2
(45) Date of Patent: Nov. 12, 2019

(54) USE OF GENINSTEIN

(71) Applicant: DSM IP ASSETS B.V., Heerlen (NL)

(72) Inventors: Kevin Prudence, Binningen (CH);
Christoph Riegger, Bettingen (CH);
Wolfgang Schalch, Bottmingen (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/864,974

(22) Filed: Jan. 8, 2018

(65) Prior Publication Data

US 2018/0133193 A1    May 17, 2018

Related U.S. Application Data

(63) Continuation of application No. 12/594,284, filed as application No. PCT/EP2008/002563 on Apr. 1, 2008, now abandoned.

(30) Foreign Application Priority Data

Apr. 2, 2007 (EP) .................................. 07006833

(51) Int. Cl.
*A61K 31/352* (2006.01)
*A23L 33/105* (2016.01)

(52) U.S. Cl.
CPC .......... *A61K 31/352* (2013.01); *A23L 33/105* (2016.08)

(58) Field of Classification Search
CPC .............................. A61K 31/352; A23L 33/105
See application file for complete search history.

(56) References Cited

U.S. PATENT DOCUMENTS

| | | |
|---|---|---|
| 5,041,434 A | 8/1991 | Lubkin |
| 6,001,368 A | 12/1999 | Jenks |
| 7,635,692 B2 | 12/2009 | Krammer et al. |
| 2004/0197272 A1 | 10/2004 | Fischer et al. |
| 2004/0220116 A1 | 11/2004 | Behnam |

OTHER PUBLICATIONS

Niederkorn et al., J immunol Apr. 1, 2006, 176 (7), 3950-3957.*
International Search Report for PCT/EP2008/002563, dated Aug. 11, 2008.
Moggs, J. G. et al., "The need to decide if all estrogens are intrinsically similar", Environmental Health Perspectives, (Aug. 2004), vol. 112, No. 11, pp. 1137-1142.
Akramian, J. et al., "Estrogen therapy in keratoconjunctivitis sicca", Advances in Experimental Medicine and Biology, (1998), vol. 438, pp. 1005-1009.
McCarty et al., "Isoflavones made simple—Genistein's agonist activity for the beta-type estrogen receptor mediates their health benefits", Medicinal Hypotheses, vol. 66, No. 6, (Jan. 1, 2006), pp. 1093-1114.
Database WPI Week 200201; Accession No. 2202-003124 & JP 2001-252045, (Sep. 18, 2001).
Blades K. J. et al, "Oral antioxidant therapy for marginal dry eye", European Journal of Clinical Nutrition, vol. 55, No. 7, (Jul. 2001), pp. 589-597.

* cited by examiner

*Primary Examiner* — Zohreh A Fay
(74) *Attorney, Agent, or Firm* — Nixon & Vanderhye P.C.

(57) ABSTRACT

Use of genistein for the treatment and prevention of dry eye syndrome or LKC and corresponding compositions containing it.

19 Claims, 1 Drawing Sheet

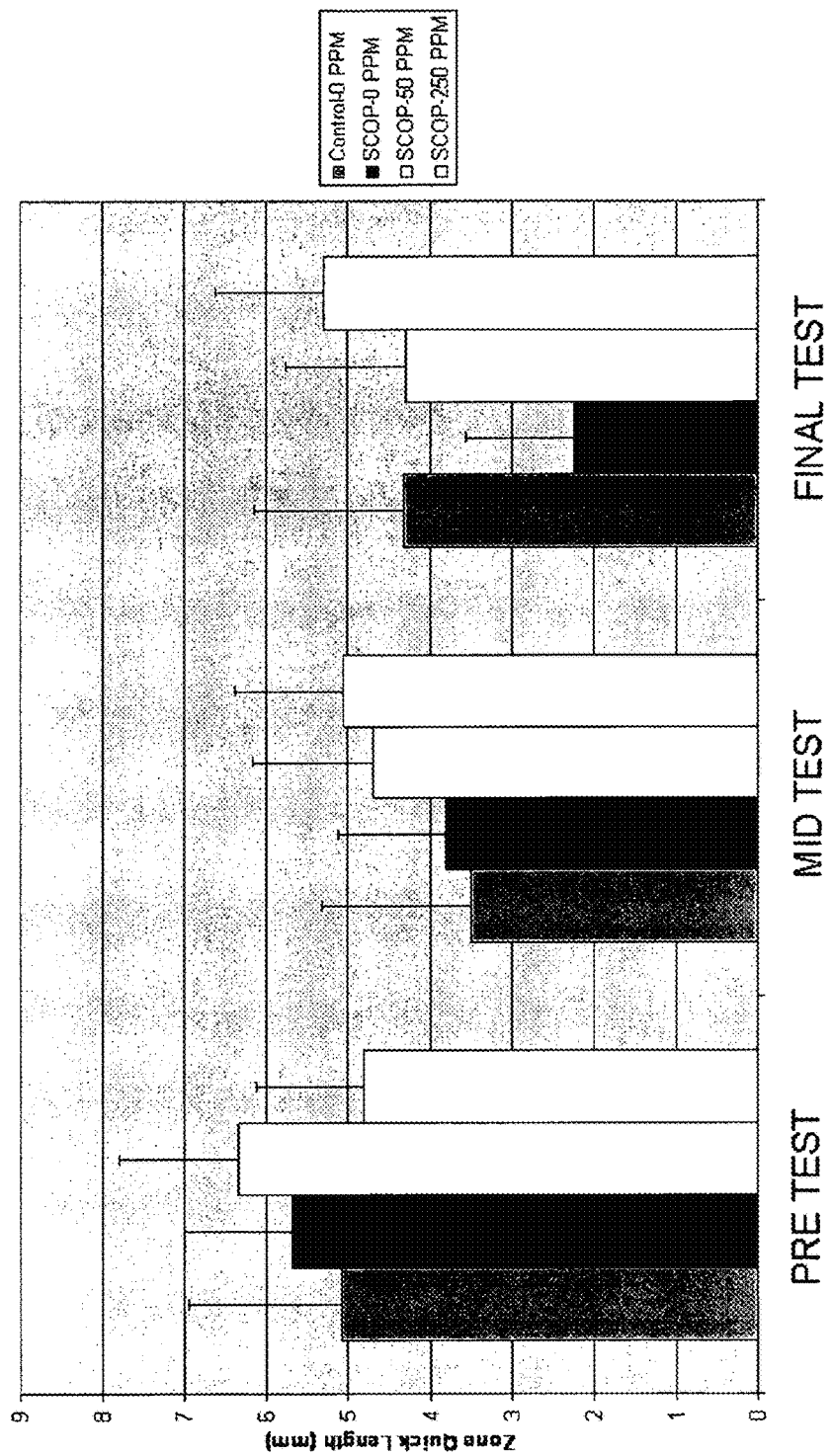

USE OF GENINSTEIN

This application is a continuation of U.S. application Ser. No. 12/594,284, filed Oct. 1, 2009, which was the U.S. national phase of International Application No. PCT/EP2008/002563 filed 1 Apr. 2008, which designated the U.S. and claims priority to Europe Application No. 07006833.3 filed 2 Apr. 2007, the entire contents of each of which are hereby incorporated by reference.

The present invention relates to a novel use of genistein and to compositions comprising it. More precisely, the present invention relates to the use of genistein and compositions containing it in the treatment and prevention of dry eye syndrome and to compositions containing it.

Dry eye was defined by the National Eye Institute (NEI)/Industry Workshop in 1993 as a "disorder" of the tear film due to tear deficiency or excessive evaporation, which causes damage to the interpalpebral ocular surface and is associated with symptoms of discomfort (Lemp, M. A.: CLAO J. 1995, 21: 221-232). Based on current knowledge of dry eye, it is also appropriate to consider it as an ocular surface inflammatory syndrome rather than simply a tear insufficiency. The term keratoconjunctivitis sicca (KCS), used for decades to describe the ocular surface disease that develops in dry eye, by definition already acknowledges an inflammatory etiology. Therefore, in keeping with a broader definition of dry eye, the term lacrimal keratoconjunctivitis (LKC) seems more appropriate and is widely used today to describe the ocular surface inflammation that develops from tear film failure (see, e.g., Pflugfelder, S. C.: "Dry eye: The problem" in Dry Eye and Ocular Surface Disorders, Marcel Decker, New York, 2004, 1-10).

Since LKC has multifactorial causes, various, allegedly promising new treatments have been suggested, e.g., novel tear stimulants and immunomodulatory agents (see review by Albietz, J. M., Clin. Exp. Optom. 84, 4-18, 2001), none of which, however, with really good results. Still in 2005 the therapy of dry eye syndrome is regarded to be one of the most frustrating clinical problems in daily ophthalmic practice (Versura, P. et al., Gynecol. Endcrinol. 20, 289-298, 2005). While many chemical compounds have been suggested to be effective and compositions containing them are commercially available, there is still an active search for a substance able to stimulate lacrimal glands to produce quantitatively and qualitatively normal tears without causing side-effects. Versura et al. also report that hormone replacement treatment (HRT) of postmenopausal women with ocular discomfort symptoms is discussed controversially and caution is recommended in rescribing HRT as therapy for dry eyes because it is not clear whether estrogen or androgen deficiency or their imbalance impairs ocular surface function.

It is, therefore, surprising that the applicants have now found that genistein, a compound naturally occurring in plants and known to have estrogenic activity, can be used in the treatment of LKC. The possibility of using genistein has not yet been proposed, although the idea of estrogens and androgens as a systemic treatment has been discussed (Scott, G. et al., Am. J. Ophthalmol. 39, 1109-10, 2005).

Genistein receptors have been found in the thymus, causing them to be effective in immune system regulation (Cooke, P. S., et al.; J. Nutr. 136, 704-8, 2006). Genistein has also been noted to affect the androgen/estrogen-induced signaling pathways via gene response modulation (Takahashi, Y., et al., Mol. Carcinog. 45, 18-25, 2006) and genistein has been found to have specific ocular activity by virtue of its inhibitory effects of ocular neovascularization (Kruse, F. E., et al., Ophthalmology 94, 152-6, 1997).

Thus, the demonstrated activity of the phyto-estrogen genistein as a modulatory agent of both the immune system and androgen-estrogen signaling, together with its parallel activity against neovascularization, as well as the presence of sex steroid receptors in the ocular surface are demonstrative of the surprising and previously unreported activity of genistein in the treatment and prevention of dry eyes.

The present invention, therefore, relates to the use of genistein in the treatment and prevention of dry eye syndrome or of LKC or in the manufacture of compositions useful in the treatment and prevention of dry eye syndrome or of LKC in a human or animal; to a method of treatment and prevention of dry eye syndrome or of LKC in humans or animals and to corresponding compositions, preferably for oral application, containing an effective amount of genistein.

The term "genistein" in the context of the present invention relates to 4',5,7-trihydroxy-isoflavone and comprises this compound in all forms, i.e., in free form or as salts, and from all sources, i.e. irrespective of whether it is prepared synthetically, by genetic engineering and expression from microorganisms or isolated from natural sources and in more or less concentrated and purified form. The term "genistein" in the context of the present invention also relates to biologically equivalent derivatives of genistein, i.e., compounds derived from genistein, occurring in nature, i.e. in natural sources or as metabolites in metabolic pathways, such as glycosides, e.g., genistin, or as glucuronides, or compounds obtainable from genistein by chemical modification or synthesis. All derivatives are included which are biologically equivalent to genistein, which means that in the organism to which they are applied they are transformed into the pharmacologically active form of genistein.

The genistein-containing compositions and application forms of the present invention are those which are generally known in the art and already used for the treatment and prevention of other medical indications and diseases. Such compositions comprise preparations for systemic, e.g., oral or parenteral but also for local and topical applications in the form of pharmaceutical as well as nutraceutical preparations, such as tablets, capsules, eye drops, ointments, gels, patches or sprays and other galenical dosage forms; solutions, concentrates and premixes for food or feed supplementation, and all kinds of food or feed themselves, including beverages.

The term "animals" comprises all animals which may suffer from dry eye syndrome or LKC, especially mammals, preferably farm animals, such as ruminants, horses and pigs; pets, such as cats and dogs, and animals kept in zoological gardens.

Suitable doses and dosage regimens can be determined by conventional range-finding techniques known to those of ordinary skill in the art. For the new use of genistein a typical range of daily administration is from about 1 to about 500 mg, preferably from about 5 to about 100 mg, if administered systemically. Topical, especially ocular administration, e.g., in the form of eye drops, eye emulsions and eye sprays, typically will involve the administration of from about 0.1 mg total to about 5 mg total, preferably 0.5-1 mg total, of genistein. Typical solutions for topical use contain genistein in a concentration of 0.0025-5%, preferably at least 0.01% and preferably up to 1%, more preferably up to 0.5%, most preferably up to 0.05%, w/v. A preferred concentration is 100 μM. In case of genistein derivatives these values have to be adapted corresponding to their bioavailabilities compared with the bioavailability of genistein itself. More details on suitable formulations in case of pharmaceutical compositions of genistein in its present new use are available from existing literature, e.g., WO 99/45920 or WO 98/26784.

Pharmaceutical compositions containing genistein can be prepared by procedures known in the art. For example, genistein can be formulated into tablets, capsules, powders, suspensions, solutions for parenteral and topical administration including intravenous, intramuscular, and subcutaneous administration, and into solutions for application onto patches for transdermal application with common and conventional carriers, binders, diluents, and excipients. In a preferred embodiment, a pharmaceutical formulation for use in the methods of the present invention includes a genistein which is at least 40% pure, preferably at least 85% pure. Inert pharmaceutically acceptable carriers useful to form pharmaceutical formulations include starch, mannitol, calcium sulfate, dicalcium phosphate, magnesium stearate, silicic derivatives, and/or sugars such as sucrose, lactose, and glucose. Binding agents include carboxymethyl cellulose and other cellulose derivatives, gelatin, natural and synthetic gums including alginates such as sodium alginate, polytheylene glycol, waxes and the like. Diluents useful in the invention include a suitable oil, saline, sugar solutions such as aqueous dextrose or aqueous glucose, and glycols such as polyethylene or polypropylene glycol. Other excipients include lubricants such as sodium oleate, sodium acetate, sodium stearate, sodium chloride, sodium benzoate, talc, magnesium stearate, and the like; disintegrating agents including agar, calcium carbonate, sodium bicarbonate, starch, xanthan gum, and the like; and adsorptive carriers such as bentonite and kaolin. Coloring and flavoring agents may also be added to the pharmaceutical formulations.

Use of genistein in nutrient formulations, dietary compositions or functional foods is achieved in accordance with methods known in the art, described, e.g., in WO 2005/063223 or U.S. Pat. No. 6,001,368.

A dietary composition in accordance with the method of the present invention is a food or feed ingredient or a food or feed containing genistein and can be prepared by adding genistein to a food or a food ingredient in the process of preparing a food, independent of the source from which the genistein is derived. The foods and feeds to which genistein compounds may be added include almost all foods and feeds including beverages and drinking water. For example, the genistein can be added to foods including, but not limited to, meats such as ground meats, emulsified meats, marinated meats, dried meats and sausages; functional foods; beverages such as nutritional beverages, sports beverages, protein fortified beverages, lemonades, juices, mineral waters, dairy products, milk, milk alternatives, and weight loss or energizing beverages; cheeses such as hard and soft cheeses, cream cheese, and cottage cheese; frozen desserts such as ice cream, ice milk, low fat frozen desserts, and non-dairy frozen desserts; yogurts; soups; puddings; bakery products; cakes and cookies; salad dressings; dips and spreads such as mayonnaise and chip dips; and extruded snack products. The genistein is added to the food in an amount selected to deliver a desired dose of it to the consumer of the food. In a preferred embodiment, a genistein composition to be added to a food for use as a dietary composition in accordance with the methods of the present invention contains at least 40% genistein preferably at least 85% genistein.

Testing the effectiveness of genistein as a treatment for the dry eye syndrome has been done using known animal models for this condition as follows:

The OVX Model:

Ovarectomized (OVX) female Sprague-Dawley rats (120-160 g) are a model for the condition of human menopause (Pflugfelder, S. C. et al. Dry eye and ocular surface disorders. Marcel Dekker, New York, 2004) and, therefore, serve as a natural model of dry eye surface disease. In addition, OVX animals may be treated with subcutaneous estradiol in order to compare the effect of this hormone replacement to treatment with genistein.

Scopolamine Model:

Another well-accepted model of dry eye is the scopolamine model which utilizes subcutaneous injections (5 mg in 10 ml) or dermal patch or gel dosage (Durson et al., Invest. Ophthalmol. Vis. Sci. 43: 632-8, 2002) of scopolamine to induce a dry eye condition in rats by parasympatholytic blockade of natural tear production.

These models and their variations were used to test the efficacy of genistein, delivered as a feed admixture (50 mg/kg low dose and 250 mg/kg high dose) to ameliorate the effects of dry eye. In addition, one test group served as a control group, receiving vehicle feed only with no added isoflavonoids.

Test animal groups were populated with equal numbers of animals (rats) as follows:

| Dry eye test groups: | |
|---|---|
| OVX: | High dose genistein |
|  | Low dose genistein |
|  | Vehicle - No isoflavonoids |
| Scopolamine: | High dose genistein |
|  | Low dose genistein |
|  | Vehicle - No isoflavonoids |
| Control groups | |
| Positive controls: | OVX Estradiol injections |
|  | High dose genistein |
|  | Low dose genistein |
|  | Vehicle - No isoflavonoids |
| Negative controls: | Wild type |
|  | Vehicle - No isoflavonoids |

Clinical in-life testing of animals supplemented with genistein or vehicle in order to assess the effect of genistein was accomplished by ocular examination with a slit lamp biomicroscope using the surface dyes fluorescein and rose Bengal.

Fluorescein was used to observe any local corneal epithelial cell loss, visible as punctuate staining as well as any breakdown in epithelial integrity as evidenced by interstitial staining. Fluorescein was also used to measure the length of time to the break-up (Tear Break Up Time—TBUT) of the tear film, which is a measure of evaporation. The normal range of TBUT is 10 seconds, but comparison of experimental vs. control animals was the primary outcome comparison.

Rose Bengal is an organic lipid dye which stains a native cell membrane and is, therefore, used to detect corneal epithelial cells that have an inadequate wetting process. The outcome measure for rose Bengal staining was any positive staining especially in comparison to control animal examinations.

Tear volume was assessed by using absorptive threads impregnated with Phenol Red (zone quick test). Outcome measures are according to criteria published in test instructions as well as comparison with control animal results.

FIG. 1 demonstrates the effects of genistein supplementation on tear production in rats treated with scopolamine, an established animal model to study the Dry Eye Syndrome. Tear volume was monitored by the Zone Quick test. This in-life test is a standardized measure of tear production. It consists of a thread impregnated with phenol red which causes a colour change of the length of the thread that becomes wet from tears when the thread is applied to the lacrimal lake. The length (in mm) of the wetted thread is proportional to the tear volume produced.

Abbreviations:

0-CON, 0-SCOP: each 8 control animals (not on scopolamine or on scopolamine)

50-SCOP: 8 animals (on scopolamine) suppl. with 50 ppm genistein

250-SCOP: 8 animals (on scopolamine) suppl. with 250 ppm genistein

MIDTEST=supplementation period 2.5 weeks

FINALTEST=supplementation period 5.0 weeks

Results:

As can be seen, supplementation of scopolamine treated rats with genistein restored their tear volume almost to control values, a tendency that that was more pronounced in the group supplemented with 250 mg than in that with 50 mg, indicating the probable existence of a dose response relationship.

The invention claimed is:

1. A method of inducing tear production in a subject having dry eye syndrome or lachrymal kerato-conjunctivitis (LCK) by ocular administering to a subject in need thereof an effective amount of a composition comprising genistein, wherein the composition is in the form of an eye drop, eye emulsion or eye spray.

2. The method of claim 1, wherein the composition contains genistein as the sole active ingredient.

3. The method of claim 1, wherein the method comprises ocular administering from about 0.1 to 5 mg of genistein.

4. The method of claim 1, wherein the method comprises ocular administering from about 0.5 to 1 mg of genistein.

5. The method of claim 1, wherein the composition comprises 0.0025% to 5% genistein.

6. The method of claim 1, wherein the composition comprises 0.01% to 1% genistein.

7. The method of claim 1, wherein the composition comprises 0.01% to 0.5% genistein.

8. The method of claim 1, wherein the composition comprises 0.01% to 0.05% genistein.

9. The method of claim 1, wherein the subject has dry eye syndrome.

10. The method of claim 1, wherein the subject has lachrymal kerato-conjunctivitis (LCK).

11. A method of inducing tear production in a subject having dry eye syndrome or lachrymal kerato-conjunctivitis (LCK) by ocular administering to a subject in need thereof an effective amount of a composition comprising from about 0.1 to 5 mg of genistein.

12. The method of claim 11, wherein the composition contains genistein as the sole active ingredient.

13. The method of claim 11, wherein the method comprises ocular administering from about 0.5 to 1 mg of genistein.

14. The method of claim 11, wherein the composition comprises 0.0025% to 5% genistein.

15. The method of claim 11, wherein the composition comprises 0.01% to 1% genistein.

16. The method of claim 11, wherein the composition comprises 0.01% to 0.5% genistein.

17. The method of claim 11, wherein the composition comprises 0.01% to 0.05% genistein.

18. The method of claim 11, wherein the subject has dry eye syndrome.

19. The method of claim 11, wherein the subject has lachrymal kerato-conjunctivitis (LCK).

* * * * *